United States Patent [19]

Cortese et al.

[11] Patent Number: 4,608,048

[45] Date of Patent: Aug. 26, 1986

[54] DISPENSING DEVICE WITH DRUG DELIVERY PATTERNS

[75] Inventors: Richard Cortese, Los Gatos; Felix Theeuwes, Los Altos, both of Calif.

[73] Assignee: ALZA Corporation, Palo Alto, Calif.

[21] Appl. No.: 678,744

[22] Filed: Dec. 6, 1984

[51] Int. Cl.[4] ............................................. A61M 7/00
[52] U.S. Cl. ................................. 604/890; 604/891; 604/892; 604/893; 604/894; 604/895; 604/896
[58] Field of Search ................................. 604/890–896

[56] References Cited

U.S. PATENT DOCUMENTS

4,210,139 7/1980 Higuchi .............................. 604/892

Primary Examiner—John Kight
Assistant Examiner—M. L. Moore
Attorney, Agent, or Firm—Paul L. Sabatine; Edward L. Mandell; Steven F. Stone

[57] ABSTRACT

An osmotic device is disclosed for delivering an agent to a selected environment. The device comprises a semipermeable wall surrounding a first and second compartment for containing the agent, and the device is provided with means for delivering the agent from both compartments through a single osmotic passageway.

29 Claims, 9 Drawing Figures

DISPENSING DEVICE WITH DRUG DELIVERY PATTERNS

FIELD OF THE INVENTION

The present invention pertains to both a novel and useful osmotic device. More particularly, the invention relates to an osmotic device for (1) delivering a first drug to a preselected region of the gastrointestinal tract, for (2) delivering consecutively a second and different drug to a different region of the gastrointestinal tract, or (3) delivering a single drug to a preselected region of the gastrointestinal tract. The invention concerns also a method for delivering a drug to a preselected region of the gastrointestinal tract.

BACKGROUND OF THE INVENTION

Both pharmacy and medicine, since the beginning of antiquity, sought a drug delivery system for the controlled administration of a beneficial drug to a warm-blooded animal. The first written reference to a drug delivery system, a dosage form, is in the Eber Papyrus, written about 1552 B.C. The Eber Papyrus mentions dosage forms such as anal suppositories, vaginal pessaries, ointments, oral pill formulations, and other dosage preparations. About 2500 years passed without any advance in dosage form development, until the Arab physician Rhazes, 865-925 A.D., invented the coated pill. About a century later the Persian Avicenna, 980-1037 A.D., coated pills with gold or silver for increasing patient acceptability and for enhancing the effectiveness of the drug. Also, around this time the first tablet was described in Arabian manuscripts written by Al-Zahrawi, 936-1009 A.D. The manuscripts described a tablet formed from the hollow impressions in two matched-facing tablet molds. Pharmacy and medicine waited about 800 years for the next innovation in dosage forms, when in 1883 Mothes invented the capsule for administering drug. The next quantum and profound leap in dosage forms came in 1972 with the invention of the osmotic delivery device by inventors Theeuwes and Higuchi. This unique osmotic delivery device is manufactured in one embodiment for oral use, and in this embodiment it embraces the appearance of a tablet with an osmotically calibrated drug delivery portal. It is the first oral dosage form in the history of pharmacy and medicine that delivers a known amount of drug per unit time at a controlled rate of delivery throughout the entire gastrointestinal tract. The oral osmotic device maintains its physical and chemical integrity during the prolonged period of time it transits the total length of the gastrointestinal tract.

The oral route is the most ancient route of drug administration, and it is the most convenient route for admitting a drug into the gastrointestinal tract for producing a local or a systemic effect. The oral route can be used for administering drugs that are used topically or absorbed into the systemic circulation from all regions of the gastrointestinal tract including the stomach, the small intestine, and the colon. The presently available oral, osmotic devices seemingly lack an apparent ability to deliver a drug to a selected region. That is, they are made to deliver drugs to all regions of the gastrointestinal tract.

It will be appreciated by those versed in the oral dispensing art, in view of this presentation, that a critical and an urgent need exists for an osmotic device that can deliver a drug only to certain regions of the gastrointestinal tract. The need exists for an oral osmotic device that can deliver a drug to certain regions of the gastrointestinal tract comprising the stomach and the small intestine for topical use or for absorption in these regions. The need exists also for an osmotic device that delivers drug only for topical application and for drug absorption in the colon. Such an osmotic device delays the onset of drug delivery for a period of time for the osmotic system to reach the latter region.

OBJECTS OF THE INVENTION

Accordingly, in view of the above presentation, it is an immediate object of this invention to provide both a novel and useful oral, osmotic drug delivery device that fulfills the critical and urgent need of the dispensing art, and also makes a substantial contribution to the dispensing art by providing a delivery system useful for obtaining better therapy in the management of health and disease.

Another object of the invention is to provide an oral osmotic drug delivery device that delivers sequentially a first drug and then delivers a second drug to the gastrointestinal tract.

Another object of the invention is to provide an oral osmotic drug delivery device that delivers sequentially a first drug to the stomach and the small intestine, and then delivers a second drug to the colon.

Another object of this invention is to provide an oral, osmotic drug delivery device that delivers a drug at a controlled rate consisting essentially of a known amount per unit time to the stomach and to the small intestine, and then delivers a different drug at a controlled rate consisting essentially of a known amount per unit time to the colon.

Another object of the invention is to provide an osmotic delivery system for the controlled delivery of a beneficial agent to the colon, and which delivery system represents an advancement in colon-specific therapy.

Another object of this invention is to provide an oral, osmotic delivery system nanufactured in the form of an osmotic device for dispensing a beneficial agent to the colon of the gastrointestinal tract of an animal for both topical and systemic therapy.

Another object of the invention is to provide an oral, osmotic device comprising an internal lumen consisting of a first and second area for housing a first and second agent in each area, said areas separated by a film having a low breakthrough pressure for releasing the second agent from the second area.

Another object of the invention is to provide an oral, osmotic device comprising an inner semipermeable wall surrounding an internal lumen comprising a first and second agent housing area separated by a film having a low breakthrough point, an outer wall formed of an enteric composition, and an osmotic passageway through the wall connecting the outside of the osmotic device with the first area for delivering the agents from the osmotic device.

Another object of the invention is to provide a method for delivering a beneficial drug to selected regions of the gastrointestinal tract.

Other objects, features, aspects and advantages of this invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and in the specification, like parts in related figures are illustrated by like numbers. The terms appearing earlier in the specifications, and in the description of the drawing figures, as well as embodiments thereof, are further described in detail throughout this specification.

DETAILED DESCRIPTION OF THE DRAWING FIGURES

Turning now to the drawing figures in detail, which drawing figures are an example of the oral, osmotic device provided by the invention, and which example is not to be construed as limiting, examples of the osmotic devices are seen in FIGS. 1 to 9 considered together.

Figure 1:
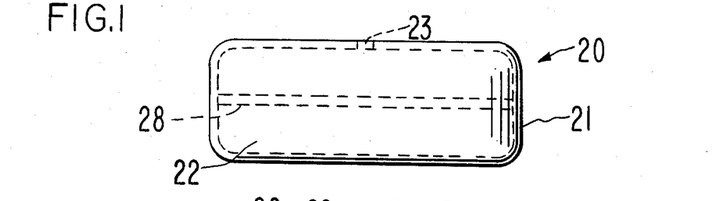
FIG. 1 is a view of an osmotic dispensing system designed for orally administering a beneficial agent such as a drug to a selected region of the gastrointestinal tract.

FIG. 1 illustrates an oral, osmotic device 20 provided by the invention. Osmotic device 20 comprises a body 21 shaped, sized and adapted for oral admittance into the gastrointestinal tract and it has a wall 22 that surrounds an internal compartment separated by a film 28, in dash lines, as seen in more detail in later figures. An osmotically dimensioned passageway 23 through wall 22 connects the exterior of osmotic dispenser 20 with the interior of osmotic dispenser 20.

Figure 2:
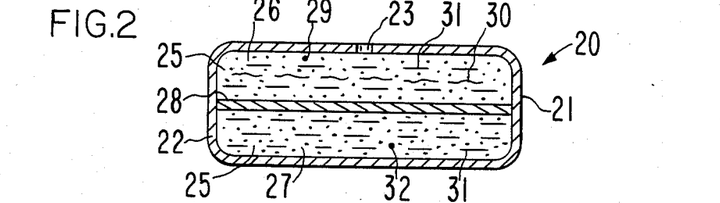
FIG. 2 is an opened view of the osmotic dispensing system of FIG. 1, depicting an embodiment of the invention comprising a semipermeable wall that surrounds and forms an internal lumen comprising a first area and a second area separated by an internal film having an in situ aperature forming ability, with a calibrated osmotic passageway in the wall connecting the first area with the exterior of the osmotic device.

FIG. 2 depicts the osmotic device of FIG. 2 in opened section. In FIG. 2, osmotic device 20 is seen with a portion of its wall 22 cut away for illustrating the internal structure of osmotic device 20. Osmotic device 20 comprises a composite wall 22 formed of semipermeable polymer composition that surrounds and forms an internal lumen 25. Semipermeable polymeric composite wall 22 is permeable to the passage of a exterior fluid present in the environment of use and it is substantially impermeable to the passage of drugs and other compounds present in osmotic device 20. Internal lumen 25 is divided into a first area 26 or first compartment and into a second area 27 or second compartment. First compartment 26 is separated from second compartment 27 by a film 28.

First compartment 26 houses, in one embodiment a beneficial drug 29, identified by dots, that is preferably soluble in an external fluid that is imbibed into compartment 26, and it exhibits an osmotic pressure gradient across wall 22 against an external fluid. Drug 29 preferably is topically useful in the stomach and in the small intestine, or drug 29 preferably exhibits its maximum absorption in the stomach and in the small intestine consisting of the duodenum, jejunum and the ileum. First compartment 26 houses, in another embodiment, an osmotically effective compound 30, identified by a wavy line. Osmotically effective compound 30 is an osmotically effective solute and it is a nontherapeutic. Osmotically effective compound 30 is soluble in an external fluid 31, identified by dashes, and it exhibits an osmotic pressure gradient across wall 22 against an external fluid. Second compartment 27 houses a beneficial drug 32 that is in a presently preferred embodiment a different drug that possesses a different therapeutic benefit than drug 29 present in first compartment 26. Beneficial drug 32 is preferably soluble in an external fluid that is imbibed into second compartment 27 through the semipermeable wall 22. Beneficial drug 32 exhibits an osmotic pressure gradient across wall 22 against an external fluid present in the environment of use. Beneficial drug 32, in one embodiment, is preferably a colon-specific drug and on its release from osmotic system 20, it produces a local or a systemic beneficial therapeutic effect in the colon.

Film 28 separates the first compartment 26 from the second compartment 27. Film 28 is a means for separating the first compartment 26 from the second compartment 27 and it enables device 20 to have different release rate patterns, and it enables device 20 to release two different agents sequentially. Film 28 delays the release of an active agent from compartment 27 until the agent present in compartment 26 is released from device 20. Film 28 also is a means for releasing agent 32 from second compartment 27, as it possesses the ability to form an aperture for releasing agent 32 from compartment 27 for agent 32 to release through osmotic passageway 23. Film 28 possesses mechanical properties that are conducive to aperture formation in response to film 28 break through pressure. The mechanical properties of film 28 include a low degree of elongation, a low tensile stength, a high degree of rupturability, a low degree of intramolecular cohesive forces, and weak intramolecular van der Waal's forces.

In operation, device 20 imbibes fluid into compartment 27 causing it to fill and apply pressure against film 28. This internal, hydrodynamic fluidic pressure urges film 28 to move towards passageway 23 and it also urges film 28 to form an aperture in direct response to its break through pressure. In operation film 28 moves towards passageway 23 as compartment 26 delivers drug 29 in response to osmotic water influx in compartment 27, when film 28 meets passageway 23, the pressure inside compartment 27 rises to a value defined as the yield pressure, YP, beyond which film 28 yields, and forms an aperture in situ, which supplies drug 32 to passageway 23, and it preferably is in alignment with passageway 23 thereby letting agent 32 present in the lower second compartment be delivered through passageway 23 from device 20. The membrane 22 has a burst pressure, BP, defined by the its properties, geometry and thickness as set forth by equation (1), $$BP = \sigma_T(h/R) \qquad (1)$$

wherein:
$\sigma_t$: tensile strength of the film
R: the radius of the osmotic device, and,
h: the film thickness The film should, therefore, be designed such that the yield pressure is smaller than the burst pressure, such that delivery occurs before significant deformation of the system occurs.

$$YP < BP \qquad (2)$$

The yield pressure can be determined from Poiseuille's law given by equation (3):

$$\frac{dv}{dt} = \frac{(YP - Pe) r^4}{8 \eta h} \qquad (3)$$

wherein:
r: radius of the delivery aperture formed in the film
$\eta$: viscosity of the partition film,
Pe: pressure exerted against the film, and,
dv/dt: the total volumetric delivery rate designated for the osmotic system.

Film 28 can be formed from hydrophobic, hydrophilic materials, including polymeric materials. Materials operable for forming film 28 are presented later in the specification.

Figure 3:
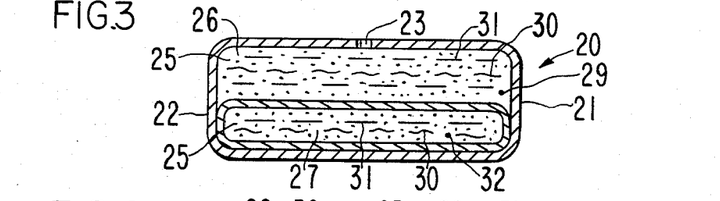
FIG. 3 is an opened view of the osmotic dispensing system of FIG. 1, depicting an embodiment of the invention comprising a semipermeable wall surrounding an internal lumen comprising a first agent containing area, and a second agent containing area surrounded by an innermost wall.

FIG. 3 depicts another embodiment of osmotic device 20 provided by the invention. In FIG. 3, the second compartment 27 is completely surrounded by film 28, which in the illustrated embodiment defines and forms compartment 27. In this manufacture, film 28 is permeable to the passage of an external fluid 31 and it is impermeable to the passage of drug 32 and osmotically effective solute 30. The osmotic device of FIG. 3 operates as described above.

Figure 4:
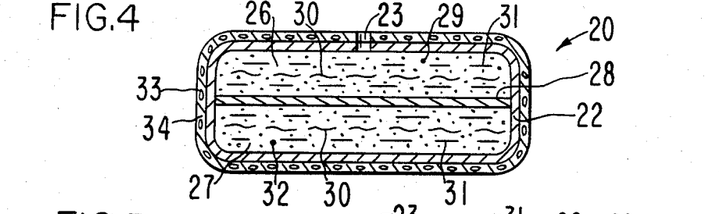
FIG. 4 depicts another embodiment of the invention comprising a laminated wall comprising a semipermeable wall in contacting laminar arrangement with a microporous lamina, which laminated wall surrounds an internal lumen divided into a first and second area separated by a film having means for forming an aperture in the film in situ during operation of the device.

FIG. 4 depicts another embodiment of osmotic device 20 provided by the invention. In FIG. 4, osmotic device 20 is made with a laminated wall 33 that surrounds the internal lumen. Laminated wall 33 comprises an exterior lamina 34 formed of a microporous material and an interior lamina 22 formed of a semipermeable material. In one operative embodiment, lamina 34 is the exterior lamina facing the environment of use, and lamina 22 is the interior lamina facing the first and second compartments. Also, in another operative embodiment, microporous limina 34 can be the interior lamina facing the first and second compartments, and semipermeable lamina 22 can be the exterior lamina facing the environment of use. Microporous lamina 34 functions as support for semipermeable lamina 22 and device 10 and it cooperates with semipermeable lamina 22 for providing fluid for imbibition into device 20.

Figure 5:
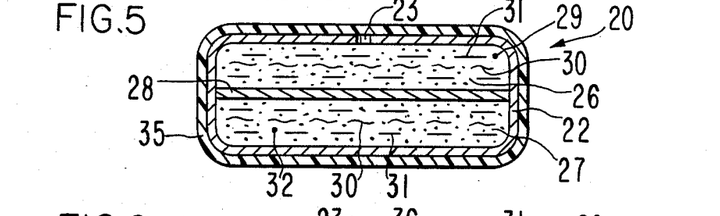
FIG. 5 depicts another embodiment of the invention comprising an osmotic device comprising an outermost enteric lamina coated onto the osmotic device.

FIG. 5 depicts another embodiment of osmotic device 20 provided by the invention. In FIG. 5, device 20 comprises an exterior lamina 35 formed of an enteric material that does not dissolve or disintegrate in the stomach during the time the osmotic system remains in the stomach, and the enteric lamina should disintegrate once the osmotic system enters the small intestine, thereby providing fluid access to semipermeable wall 22.

Figure 6:
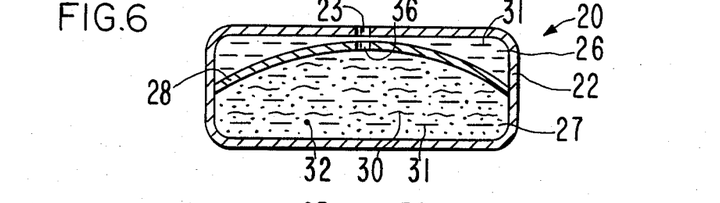
FIG. 6 is an opened view of the osmotic device of FIGS. 1 and 2 depicting the internal film with an aperture formed in situ during operation of the osmotic device.
Figure 7:
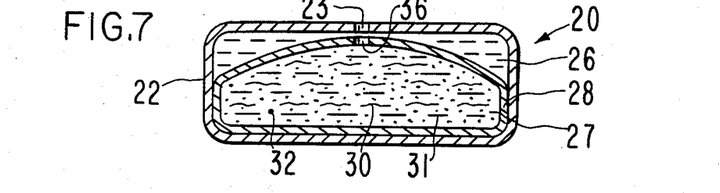
FIG. 7 is an opened view of the osmotic device of FIG. 3 illustrating the innermost wall in agent delivery position with an aperture formed in situ during the operation of the osmotic device.
Figure 8:
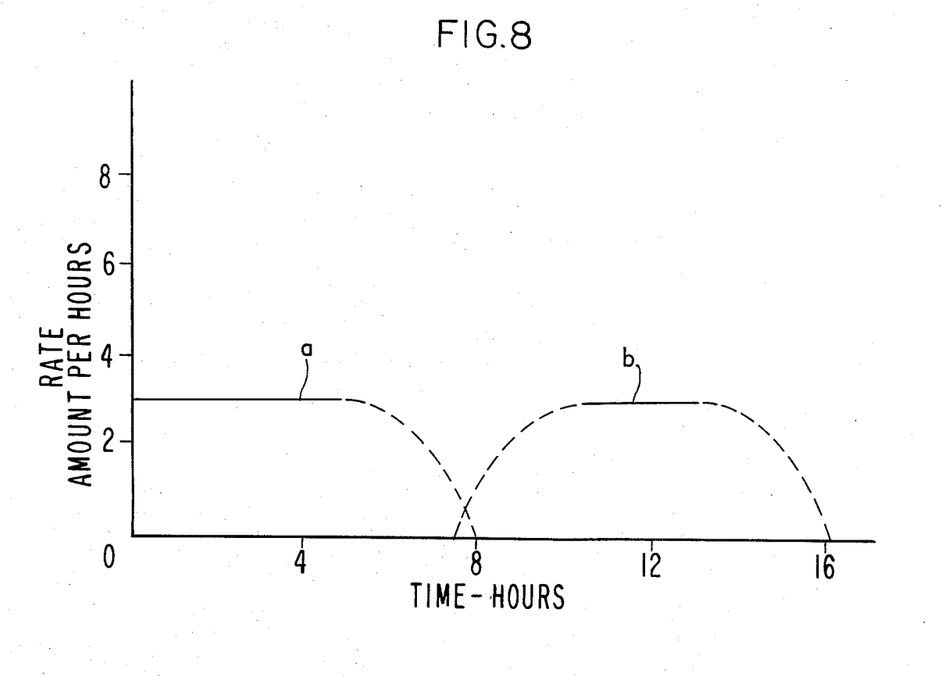
FIG. 8 is a graph that depicts the release rate pattern for an osmotic device provided by this invention, that illustrates release of a first agent followed by the independent release of the second agent from the osmotic device.
Figure 9:
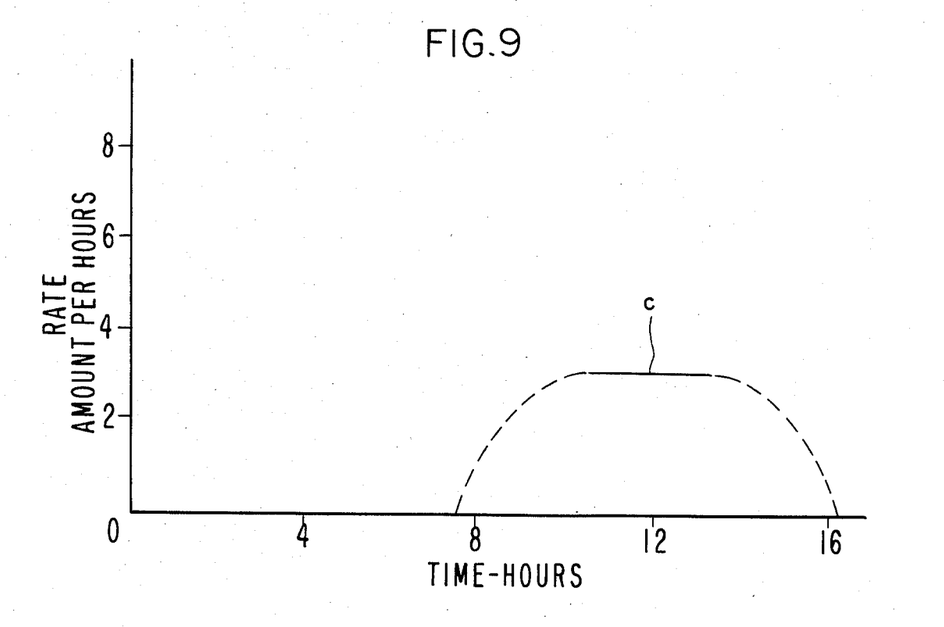
FIG. 9 is a graph that depicts the delayed release patterns for an agent from an osmotic device provided by this invention.

FIGS. 6 and 7 depict device 20 in operation in the biological environment of use and FIGS. 8 and 9 depict the results obtained by operating the osmotic device. FIG. 6 illustrates device 20 of FIG. 2 in operation, and FIG. 7 illustrates device 20 of FIG. 3 in operation as described above. That is, in operation, film 20 in both embodiments moves under pressure from a rested position to an expanded position, thereby causing film 20 to rupture in situ and form agent releasing aperture 36. Then, agent 32 present in compartment 27 is hydrodynamically dispensed through aperture 36 and through passageway 23 to the exterior of osmotic device 20. FIG. 8 depicts the release rate pattern for osmotic device 20 delivering two different active agents to the environment of use. Device 20 houses agent "a" in the first compartment and agent "b" in the second compartment. In operation, device 20 first delivers agent "a" through passageway 23 with film 28 simultaneously moving towards passageway 23 like a piston or elongating in an arc-like manner. In time, agent "a" is delivered from device 20 with film 28 concomitantly arriving at passageway 23 and forming aperture 36, thereby enabling agent "b" to be delivered from device 20. FIG. 9 illustrates a different delivery profile for device 20. In this embodiment, the first compartment houses a non-therapeutic agent that is delivered from device 20 followed by the delivery of an active agent "c" from the second compartment. The latter delivery profile provides delayed delivery for releasing the active agent in the colon.

Osmotic delivery system 20 as seen in FIG. 1 through 7 can be made into many embodiments for oral use for releasing locally or systemically acting therapeutic medicaments in the gastrointestinal tract. The oral system can have various conventional shapes and sizes such as round with a diameter of ⅛ inch to 9/16 inch, or it can be shaped like a capsule having a range of sizes from triple zero to zero and from 1 to 8. In these manufactures, system 20 can be adapted for administering a beneficial agent to warm-blooded mammals such as humans.

DETAILED DESCRIPTION OF THE INVENTION

In accordance with the practice of this invention, semipermeable wall 22 is formed of a material that does not adversely affect the beneficial agent and the animal host. The semipermeable wall forming material is a polymer that is permeable to the passage of an external fluid such as water and aqueous biological fluids, while remaining substantially impermeable to beneficial agents and osmotic solutes. The selectively permeable materials forming semipermeable lamina 22 are materials that are insoluble in body fluids and they are non-erodible. Typical selective materials for forming wall 22 include semipermeable polymers, also known to the art as osmosis membranes. The semipermeable polymers include cellulose acrylate, cellulose, diacylate, cellulose triacylate, cellulose ester, cellulose ether, and cellulose ester ether. Representative semipermeable polymers include cellulose acetate, cellulose diacetate, cellulose triacetate, dimethylcellulose acetate, cellulose acetate propionate, cellulose acetate butyrate, and the like. Semipermeable polymers are known in U.S. Pat. Nos. 3,173,876; 3,276,586; 3,541,005; 3,541,006; 3,546,142; 3,845,770; 3,916,899; 4,036,288; and 4,111,202.

The microporous materials comprising microporous lamina 34 maintains their physical and chemical integrity during the period of time drug is released from system 20. The microporous materials comprising lamina 34 generally can be described as having a sponge-like appearance that provides a supporting structure for microscopic sized interconnected pores or voids. The materials can be isotropic wherein the structure is homogeneous throughout a cross-sectional area, or the materials can be anisotropic wherein the structure is non-homogeneous throughout a cross-sectional area, or the materials can have both cross-sectional areas. The materials are opened-celled, as the micropores are continuous or connected, with pores having an opening on both faces of the microporous lamina. The micropores are interconnected through tortuous paths of regular and irregular shapes including linear, curved, curved-linear, randomly oriented continuous pores, hindered connected pores, and other interconnected porous paths discernible by microporous examination.

Generally, the microporous lamina is characterized as having a reduced bulk density as compared to the bulk density of the corresponding non-porous microporous lamina. The morphological structure of the total microporous wall have a greater proportion of total surface area than the non-porous wall. The microporous wall can be further characterized by the pores size, the number of pores, the tortuosity of the microporous paths, and the porosity which relates to the size and the number of pores. Generally, material possessing from 5% to 95% pores, and having a pore size of from 10 angstroms to 100 microns can be used for making the microporous lamina.

Materials useful for making the microporous lamina include microporous polycarbonates comprised of linear polyesters of carbonic acid in which carbonate groups recur in the polymer chain, microporous materials prepared by the phosgenation of a dihydroxyl aromatic such as bisphenol, a microporous poly(vinylchloride), microporous polyamides such as polyhexamethylene adipamide, microporous modacrylic copolymers including those formed from poly(vinylchloride) and acrylonitrile, microporous styrene-acrylic and its copolymers, porous polysulfones characterized by diphenylene sulfone in a linear chain thereof, microporous halogenated poly(vinylidene), microporous polychloroethers, microporous acetal polymers, microporous polyesters prepared by esterification of a dicarboxylic acid or anhydride with an alkylene polyol, microporous poly(alkylenesulfides), microporous phenolics, microporous polyesters, microporous polysaccharides having substituted anhydroglucose units exhibiting a decrease permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066, 3,709,774; 3,718,532; 3,803,601; 3,852,224; 3,852,388; and 3,853,601; in British Pat. No. 1,126,849; and in Chem. Abst. Vol. 71, 427F, 22573F, 1969.

Additional microporous materials for forming microporous lamina 20 include microporous poly(urethane), cross-linked chain-extended microporous poly(urethane), microporous poly(imides), microporous poly(benzimidazoles), microporous materials prepared by diffusion of multivalent cations into polyelectrolyte sols, microporous derivatives of poly(styrene) such as poly(sodium-styrene-sulfonate), poly(vinyl benzyl trimethylammonium chloride), and the like microporous polymers are known in U.S. Pat. Nos. 3,524,753; 3,565,259; 3,276,589; 3,541,055; 3,541,006; 3,546,142; 3,615,024; 3,646,178; and 3,852,224.

The pore-formers useful for forming the microporous lamina in the environment of use include solids and pore-forming liquids. The term pore-former as used herein also embraces micropath formers, and removal of the pore and/or pore-former leads to both embodiments. In the expression pore-forming liquids, the term for this invention generically embraces semisolids and viscous fluids. The pore-formers can be inorganic or organic and the lamina forming polymer usually contains from 5 to 70% by weight of the pore-former, and more preferably about 20 to 50% by weight. The term pore-former for both solids and liquids include substances that can be dissolved, extracted or leached from the precursor microporous wall by fluid present in the environment of use to form capable, open-celled type microporous lamina. The pore-forming solids have a size of about 0.1 to 200 microns and they include alkali metal salts such as lithium carbonate, sodium chloride, sodium bromide, potassium chloride, potassium sulfate, potassium phosphate, sodium acetate, sodium citrate, and the like. Organic compounds such as polysaccharides including the sugars sucrose, glucose, fructose, mannitol, mannose, galactose, sorbitol and the like. The pore-formers are non-toxic and on their removal from lamina 34, channels and pores are formed through the lamina that fill with fluid present in the environment of use.

Lamina 35 is made from enteric materials that do not dissolve or disintegrate in the stomach during the period of time the osmotic system passes through the stomach. The enteric materials suitable for forming enteric lamina 35 include: (a) enteric materials that are digestible by enzymes in the small intestine; (b) enteric materials containing an ionizable polyacid; (c) enteric materials that are a long-chain polymer with an ionizable carboxyl group, and the like. Representative enteric materials include: (d) a member selected from the group consisting essentially of cellulose acetyl phthalate, cellulose diacetyl phthalate, cellulose triacetyl phthalate, cellulose acetate phthalate, hydroxypropylmethyl cellulose phthalate, sodium cellulose acetate phthalate, cellulose ester phthalate, cellulose ether phthalate, methyl cellulose phthalate, cellulose ester-ether phthalate, hydroxypropyl cellulose phthalate, and the like; (e) a member selected from the group consisting of keratin, keratin sandarac-tolu, salol, salol α-naphthyl benzoate and acetotannin, salol with balsam of Peru, salol with tolu, salol with gum mastic, salol and stearic acid, and salol and shellac; (f) a member selected from the group consisting of formalized protein, formalized gelatin, and formalized cross-linked gelatin and exchange resins; (g) a member selected from the group consisting of myristic acid-hydrogenated castor oil-cholesterol, stearic acid-mutton tallow, stearic acid-balsam of tolu, and stearic acid-castor oil; (h) a member selected from the group consisting of shellac, ammoniated shellac, ammoniated shellac-salol, shellac-wool fate, shellac-cetyl alcohol, shellac-stearic acid-balsam of tolu, and shellac-n-butyl stearate; (i) a member selected from the group consisting of abietic acid, methyl abietate, benzoin, balsam of tolu, sandarac, mastic with tolu, and mastic with cetyl alcohol; (j) a member selected from the group consisting of cellulose acetate with shellac, starch acetate phthalate, polyvinyl acid phthalate, 2-ethoxy-5-(2-hydroxyethoxy-methyl)-cellulose phthalic acid, acid phthalates of carbohydrates, zein, alkyl resin-unsaturated fatty acids-shellac, colophonyl, mixtures of zein and carboxymethylcellulose; and the like. The enteric materials are discussed in *Remington's Pharmaceutical Sciences*, 13th Ed., pages 604–605, (1965), published by Mack Publishing Co., Eaton, PA.

Film 28 is made from a member selected from the group consisting of hydrophilic and hydrophobic film-forming materials. The hydrophilic materials suitable for forming film 28 include a member selected from the group consisting essentially of a poly(alkylene oxide) polymer of the general formula $(O-R)_n$, wherein R is a straight or a branched chain alkylene group and n is from about 200 to 150,000, exemplified by a poly(ethylene oxide) of the general formula $(O-CH_2-CH_2)_n$ have a molecular weight of from 10,000 to 5,000,000; a poly(alkylene glycol) of the general formula $HOCH_2(CH_2OCH_2)_nCH_2OH$ wherein n is 6 to 1500 and the polymers have a molecular weight of from about 1000 to 14,000; a carboxypolymethylene polymer also referred to as carboxyvinylpolymer, a polymer formed in one embodiment by cross-linking acrylic acid with a polyallyl ether of sucrose, and which generic carboxyvinylpolymers as embodied herein have a molecular weight range of from 100,000 to 400,000; film-forming acrylate polymers, methacrylate polymers and copolymers, such as polymethacrylate, polymethylmethacrylate, polymethylmethacrylate/methacrylic acid, polymethacrylate/methacrylic acid, polyacrylate/methylmethacrylate, polymethacrylate/methylmethacrylate, and the like; a film-forming ion exchange polymer such as polystyrene sulfonic acid, polystyrene divinylvenzene copolymer, copolymer of polymethacrylic and divinyl benzene, copolymer of polymethacrylic and divinyl benzene, copolymer of polyacrylic acid and divinyl benzene, sulfonated divinylbenzene-styrene copolymer, and the like. Representative hydrophobic film-formers include waxes such as ozokerite, carnauba, bayberry, flax, beeswax, and the like; triglycerides of $C_{12}$ to $C_{18}$ fatty acids, paraffin, and the like. Also, film-forming polymers such as ethylene-vinyl acetate copolymer, polyisobutylene-mineral oil complexes, silicones, and the like. Generally, the film between the first and second compartment will be from about 0.1 mm to 5 mm thick.

In the specification and the accompanying claims, the term drug includes inorganic and organic drugs that are used topically or absorbed in the stomach, the small intestine and in the colon. The drugs include drugs that act on the nervous system, depressants, hypnotics, sedatives, psychic energizers, tranquilizers, anticonvulsants, muscle relaxants, antiparkinsons, analgesics, anti-inflammatory, anesthetics, muscle contractants, antimicrobiols, antimalarials, hormones, contraceptives, sympathomimetrics, diuretics, antiparasites, neoplastics, hypoglycemics, ophthalmics, electrolytes, cardiovascular, blood pressure regulating drugs, antiulcer, histamine antagonists, and the like.

Representative of drugs that can be administered in the stomach and in the small intestine include hycanthone, aminophylline, aminosalicylic acid, sulfoxone sodium, erythromycin estolate, erythromycin, orenzme, carbomycin, riboflavin, thiamine, vitamin $D_2$, vitamin $D_3$, vitamin $B_{12}$, phenylbutazone, acetylsalicylic acid, xanthone, thioxanthone, morphine, codeine, 5-fluorouracil, 5-bromouracil, benzomethamine, oxphenonium, hexamethonium, tubocurarine, atropine, folic acid, and the like. Representative of drugs that can be administered in the colon include 5-amino-salicylic acid, sodium cefmetazole, sodium cefoxitin, mefenamic acid, carbamazepine, isoxicam, glafenini, theophylline, and the like. The amount of drug present in a device will vary depending on the activity and the amount of drug to be administered to the host. Generally, the osmotic device will contain in each compartment from 0.05 ng to 2 g, or more, with individual devices containing 5 mg, 25 mg, 50 mg, 125 mg, 250 mg, 500 mg, and the like, of a different drug in each compartment. The drugs are known in the art in *Pharmaceutical Sciences*, by Remington (1980) published by Mack Publishing Co.; *Physicians' Desk Reference*, 36th Edition, (1982) published by Medical Economics Co.,; and *Medical Chemistry*, 3rd Edition, Vol. 1 and 2, by Burger, published by Wiley-Interscience Co.

The osmotically effective compound, which is an osmotically effective solute, can be present alone in the first compartment thereby enabling the device to exhibit a delayed start for the release of drug from the second compartment; or, the osmotically effective compound can be present in either compartment as an aid for effecting the release of a drug from either compartment. Generally, the osmotically effective compound is a member selected from the group consisting of water-soluble inorganic salts and water-soluble organic salts that are selected from the group consisting of magnesium sulfate, magnesium chloride, sodium chloride, lithium chloride, potassium sulfate, sodium carbonate, sodium sulfite, lithium sulfate, sodium sulfate, potassium acid phosphate, choline chloride, and the like. The osmotically effective compounds are known to the art in U.S. Pat. Nos. 4,177,256 and 4,449,983.

The expression osmotic passageway as used herein comprises means and methods suitable for releasing a beneficial agent, or an inactive agent, from the first compartment and ultimately from the second compartment. The osmotic passageway will pass through the wall for communicating with the first compatment. The expression for passageway includes passageways formed by mechanical drilling or laser drilling through the wall. Generally, for the purpose of the invention, the passageway will have a maximum cross-sectional area, A, defined by the equation:

$$\frac{L}{F} \times \frac{Qv}{t} \times \frac{1}{DS} \qquad (1)$$

wherein L is the length of the passageway (Qv/t) is the mass delivery rate of agent D released per unit time, D is the diffusion coefficient of the agent in the release solution, S is the solubility of the agent in the fluid and F has a value of approximately 2 to 1000, said osmotic passageway having a minimum area, $A_s$, defined by the equation:

$$A_s = \left[ \frac{Lv}{t} \times 8\pi \times \frac{\eta}{\Delta P} \right]^{\frac{1}{2}} \qquad (2)$$

wherein L is the length of the passageway, v/t is the volume of the agent released per unit of time $\tau$ is 3.14, $\eta$ is the viscosity of the solution being released, and $\Delta P$ is the hydrostatic pressure difference between the inside and the outside of the compartment and having a value up to 20 atmospheres. The dimensions for the osmotic passageway is disclosed in U.S. Pat. No. 3,916,899.

The osmotic device of the invention is manufactured by standard techniques. For example, in one manufacture, a drug and optionally an osmagent, or an osmagent alone, and other compartment forming ingredients that may be housed in one compartment are mixed into a solid, semi-solid, moist, or pressed state by conventional methods such as ballmilling, calendering, stirring or rollmilling, and then pressed into a preselected shape. A film is formed by molding, spraying or dipping one surface of the pressed shape into the film forming material. The second compartment is formed by pressing a drug, or optionally a drug and an osmagent into a preselected shape that corresponds to the above formed shape, and then intimately attaching it to the film, or a drug and an osmagent can be pressed directly onto the film. Finally, the two compartments are surrounded by a semipermeable wall or they are surrounded by a laminated wall. Optionally, osmotic device can be manufactured by first fabricating one compartment by pressing in a standard tablet machine, a drug or an inactive agent such as a sugar, and while the first shaped-pressed compartment is in the table pressing machine, a layer of a film forming material is added thereto, and then the other compartment is formed by pressing drug to the first compartment. Finally, the two adjacent compartments are surrounded with a wall formed of a semipermeable material, and a passageway is drilled through the semipermeable wall into the first compartment to form osmotic device 20. The compartment also can be joined by other methods including heat sealing, pressing, consecutively casting the compartments in a dual cavity mold, overlaying, and the like.

In an embodiment, the device is made by compressing a drug, and then suspending and tumbling the drug in an interior wall forming composition until the interior wall is applied around the drug. Next, after drying, an osmotic solute is compressed against the interior wall, and the article returned to the air suspension machine, suspended and tumbled in a current of air until the external wall is formed around the two compartments. After drying, a passageway is drilled in the external wall connecting the solute compartment with the exterior of the device. Generally, the semipermeable wall will have a thickness of 2 to 20 mils, with a presently preferred thickness of 4 to 12 mils. The film between the compartments generally will have a thickness of 0.1 to 5 mil, with a presently preferred thickness of 1 to 3 mil. In laminated wall, the lamina will have a thickness of 2 to 10 mils with a presently preferred thickness of 2 to 5 mils. Of course, thinner and thicker walls, lamina and partitions for use with numerous drugs and osmagents are within the scope of the invention. The air suspension procedure is described in U.S. Pat. No. 2,799,241; in *J. Am. Pharm. Assoc.*, Vol. 48, pages 451 to 459, (1959) and ibid., Vol. 49, pages 82 to 84, (1960). Other wall forming techniques such as pan coating can be used in which materials are deposited by successive spraying of the polymer solution on the drug, or solute, accompanied by tumbling in a rotating pan. Other standard manufacturing procedures are described in *Modern Plastics Encyclopedia*, Vol. 46, pages 62 to 70, (1969); and in *Pharmaceutical Sciences*, by Remington, 14th Ed., pages 1626 to 1678, (1970) published by Mack Publishing Co., Eaton, PA.

Elemplary solvents suitable for manufacturing the walls include inert inorganic and organic solvents that do not adversely harm the wall forming materials, the drug, the agent, and the final device. The solvents broadly include aqueous solvents, alcohols, ketones, esters, ethers, aliphatic hydrocarbons, halogenated solvents, cycloaliphatic aromatics, heterocyclic solvents, and mixtures thereof. Typical solvents incluce acetone, diacetone alcohol, methanol, ethanol, isopropyl alcohol methyl acetate, ethyl acetate, methyl isobutyl ketone, n-hexane, ethylene glycol monoethyl acetate, carbon tetrachloride, methylene chloride, ethylene dichloride, propylene dichloride, cyclohexane, mixtures such as acetone and water, acetone and methanol, acetone and ethyl alcohol, methylene dichloride and methanol, ethylene dichloride and methanol, and mixtures thereof.

DESCRIPTION OF THE EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery device for the controlled delivery of the two beneficial drugs hydralazine hydrochloride and metoprolol fumarate to a biological environment of use is made as follows: first, a compartment forming composition is compounded from 50 mg of hydralazine hydrochloride, 208.5 mg of mannitol, 8 mg of hydroxypropyl methylcellulose and 8 mg of stearic acid by mixing the hydralazine hydrochloride and the mannitol and then passing the mixture through a 40-mesh screen, next, the hydroxypropyl methylcellulose is dissolved in a 70/30 (w/w%) ethanol-water solution and the hydralazine-mannitol mixture added to the wet hydroxypropyl methylcellulose and all the ingredients blended for 10 minutes. Next, the blend is passed through a 10-mesh screen and spread on a tray and dried in a forced air oven at 50° C. for 18–24 hours. The dried blend is passed through a 20-mesh screen, placed in a mixer, and the stearic added to the blend and the mixing continued for 10 minutes.

A second compartment forming composition comprised of 190 mg of metoprolol fumarate, 8.4 mg of sodium bicarbonate, 10.6 mg of polyvinyl pyrrolidone and 3.2 mg of magnesium stearate is made by first mixing the metoprolol fumarate with sodium bicarbonate and passing the mixture through a 40-mesh screen, then, the polyvinyl pyrrolidone is mixed with 15 ml of ethanol and 5 ml of water, and the freshly prepared polyvinyl pyrrolidone solution is added slowly with mixing to the metoprolol fumarate-sodium bicarbonate mixture.

The ingredients are mixed for 20 minutes, passed through a 10-mesh screen and dried in a forced air oven for 24 hours. Next, the dried blend is passed through a 20-mesh screen, placed in a mixer, the magnesium stearate added and the ingredients again blended to yield the compartment composition.

Next, 275 mg of the hydralazine drug formulation reservoir, as described above, is placed into a 7/16 inch biconvex oval tablet die, and the turret of the tablet compression machine turned until the load reaches the compression point with the drug formulation compressed into the shape of the die. The turret is reversed back to the loading position and 100 mg of film forming polyethylene oxide is spread over the compressed drug formulation to form a compartment dividing film. Next, the turret is turned to the compression point to assist in forming the film between compartments. Then, the turret is returned to the loading position, and 200 mg of the metoprolol fumarate drug formulation is added to the die in contact with the partition, and the formulation pressed against the film. The two united compartments then were coated in an air suspension machine with a wall of semipermeable cellulose acetate with a wall forming composition comprised of 43% cellulose acetate having an acetyl content of 32%, 43% cellulose acetate having an acetyl content of 39.8% and 14% hydroxypropyl methylcellulose, dissolved in an 80 to 20 parts by weight of a methylene chloride-methanol solvent. The two compartments are coated with the cellulose acetate to form a semipermeable wall having a thickness of 7 mils. The coated compartments are dried in a forced air oven at 50° C. for one week. Then, a passageway is laser drilled through the wall into the hydrazaline compartment. The passageway has a diameter of 9 mils for delivering hydrazaline from the first compartment, and upon subsequent in stiu aperture formation in the film, the metoprolol is released through the same 9 mil passageway.

EXAMPLE 2

A non-stirring rate dependent osmotic device that releases a diluted drug solution independent of the pH of the environment is manufactured as follows: first, 125 mg of the diuretic ethacrynate sodium is compressed into a solid mass in a commercially available Manesty tablet machine to a Stoke's hardness of 8 kg. Next, the solid is coated in a standard air suspension machine with a semipermeable polymer cellulose acetate having an acetyl content of 38.3%. A 90% methylene chloride 10% methanol solvent is used for forming the wall, and excess solvent is evaporated at 50° C. for 40 hours. The freshly formed wall has a thickness of 5 mils. This step provides the second compartment of a delayed delivery osmotic device.

Next, a first compartment is prepared as follows: first, 350 mg of an osmotically effective composition consisting of the biologically inert agents dextrose and fructose is pressed in the Manesty machine to a Stoke's hardness of 8 kg. The pressed composition has a shape that mates with the shape of the drug compartment to minimize air entrapment. Then, a small drop of liquid cellulose acetate dissolved in a suitable solvent is spread around the outer edge of one surface of the pressed composition, and this surface is placed against the corresponding surface of the drug compartment. The two united masses are then coated in the air suspension coater with a wall of semipermeable cellulose acetate to a thickness of 10 mils. The wall is formed from a 5% solution consisting essentially of cellulose acetate having an acetyl content of 32%. The solution is made by dissolving 155 g of cellulose acetate in a solvent consisting of 3300 ml of acetone and 330 ml of water. The acetone and water have an 88.5 to 11.5 weight to weight basis. Finally, an osmotic passageway having a diameter of 10 mils is drilled through one exterior wall facing the mixed solutes for delivering first the inactive sugars followed by the delivery of the drug from the osmotic device.

EXAMPLE 3

An osmotic device is prepared comprising a first and second compartment separated by a 3 mm film of carboxyvinyl polymer having a molecular weight of about 3,000,000. The first compartment weighs 400 mgs and it comprises 99.4 wt % of potassium chloride and 0.5 wt % magnesium stearate. The second compartment weighs 280 mgs and it comprises 93 wt % oxprenolol hydrochloride, 4 wt % poly(vinyl pyrrolidone) and 3 wt % stearic acid. The compartments are surrounded by a semipermeable wall weighing 52 mgs comprising 100 wt % cellulose acetate having an acetyl content of 39.8%. A 0.111 mm passageway connects the first compartment with the exterior of the osmotic device.

EXAMPLE 4

An osmotic device is prepared comprising a first and second compartment each containing a different drug, with the compartments separated by a 2.5 mm thick film of polyacrylamide having a molecular weight of 5 to 6 million. The first compartment weighed 400 mg and it had a drug content of 397 mg of potassium chloride and 3 mg of silicon dioxide. The second compartment weighed 268 mg and it had a drug content of 249.2 mg of oxprenolol hydrochloride, 11.7 mg of poly(vinyl pyrrolidone) and 8.1 mg of stearic acid. The compartments are separated by the film in laminar arrangement and they are surrounded by a semipermeable cellulose acetate wall having an acetyl content of 39.8%. A 0.12 mm osmotic passageway in the semipermeable wall connects the first compartment with the exterior of the osmotic device.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:
1. An osmotic device for the controlled delivery of a beneficial agent to an environment of use, comprising:
   (a) a wall comprising in at least a part a semipermeable composition permeable to the passage of an exterior fluid present in the environment of use and substantially impermeable to the passage of a beneficial agent, the wall surrounding:
   (b) a first compartment containing a beneficial drug;
   (c) a second compartment containing a beneficial drug;
   (d) at least one passageway in the wall initially communicating with the first compartment and the exterior of the device; and,
   (e) means in the device for separating the first and second compartments for initially restricting the passage of beneficial drug from the second compartmentt, said means comprising the ability for forming at least one aperture in situ for releasing the drug from the second compartment and then through the passageway that initially communicated with said first compartment for delivering the drug from the device.

2. The osmotic device for the controlled delivery of a beneficial drug according to claim 1, wherein the beneficial drug in the second compartment is a different beneficial drug than the beneficial drug in the first compartment.

3. The osmotic device for the controlled delivery of a beneficial drug according to claim 1, wherein the device delivers the beneficial drug from the first compartment followed by the delivery of the beneficial drug from the second compartment.

4. The osmotic device for the controlled delivery of a beneficial drug according to claim 1, wherein the environment of use is the gastrointestinal tract and the device delivers the beneficial drug from the first compartment to the stomach and the small intestine, and delivers the beneficial drug from the second compartment to the colon.

5. The osmotic device for the controlled delivery of a beneficial drug according to claim 1, wherein the beneficial drug in the first compartment is mixed with an osmagent.

6. The osmotic device for the controlled delivery of a beneficial drug according to claim 1, wherein the beneficial drug in the second compartment is mixed with an osmagent.

7. The osmotic device for the controlled delivery of the beneficial drug according to claim 1, wherein the wall comprises a member selected from the group consisting of cellulose acylate, cellulose diacylate, cellulose triacylate, cellulose acetate, cellulose diacetate and cellulose triacetate.

8. The osmotic device for the controlled delivery of a beneficial drug according to claim 1, wherein the means forms in situ an aperture in alignment with the passageway for delivering the beneficial drug from the second compartment to the exterior of the device.

9. The osmotic device for the controlled delivery of a beneficial drug according to claim 1, wherein the environment of use is a human.

10. An osmotic device for the controlled delivery of a therapeutically beneficial drug to an environment of use, said device comprising:
(a) a wall comprising in at least a part a semipermeable composition permeable to the passage of an exterior fluid present in a biological environment of use and substantially impermeable to the passage of a beneficial drug, said wall surrounding and defining:
(b) an internal lumen, which lumen comprises:
(1) a first area containing a nontoxic therapeutically inactive formulation;
(2) a second area containing a nontoxic therapeutically active drug formulation; and,
(3) means in the lumen for both separating the first and second area and for providing at least one orifice in the means formed in the means when the device is in operation in the environment of use for releasing the drug formulation from the second area; and,
(c) at least one passageway in the wall communicating with the first area and the exterior of the device.

11. The osmotic device for the controlled delivery of a therapeutically beneficial drug according to claim 10, wherein the environment of use is the gastrointestinal tract and the device delivers the inactive formulation to the stomach and the small intestine and delivers the active drug formulation to the colon.

12. The osmotic device for the controlled delivery of a therapeutically beneficial drug according to claim 11, wherein the means in the lumen is a film that forms a drug releasing orifice during operation of the device.

13. The osmotic device for the controlled delivery of a therapeutically beneficial drug according to claim 11, wherein the passageway originally communicates with the first area and the means forms an orifice that communicates with the passageway.

14. The osmotic device for the controlled delivery of a therapeutically beneficial drug according to claim 10, wherein the drug formulation in the second area comprises a dosage unit amount of a drug and an osmagent.

15. The osmotic device for the controlled delivery of a therapeutically beneficial drug according to claim 10, wherein the formulation in the first area comprises a therapeutically inactive osmagent.

16. The osmotic device for the controlled delivery of a therapeutically beneficial drug according to claim 10, wherein the device is sized, shaped and adapted for oral administration into the gastrointestinal tract.

17. The osmotic device for the controlled delivery of a therapeutically beneficial drug according to claim 10, wherein the formulation in the first and second area each contain a different osmagent.

18. The osmotic device for the controlled delivery of a therapeutically beneficial drug according to claim 10, wherein when the device is in operation in the environment of use, fluid from the environment is imbibed through the wall into (1) the first area in a tendency towards osmotic equilibrium at a rate determined by the permeability of the wall and the osmotic pressure gradient across the wall, thereby forming a solution that is delivered through the passageway from the device at a controlled rate over a prolonged period of time, and into (2) the second area in a tendency towards osmotic equilibrium at a rate determined by the permeability of the wall and the osmotic pressure gradient across the wall thereby forming a solution that is released by the means from the second area and delivered by the device through the passageway from the device at a controlled rate over a prolonged period of time.

19. An osmotic therapeutic device for the controlled delivery of a beneficial drug to a biological environment, the device consisting essentially of:
(a) a wall comprising in at least a part a semipermeable lamina in laminar arrangement with a lamina comprising in at least a part a microporous lamina, the laminated wall surrounding and forming:
(b) a first compartment comprising a drug formulation that exhibits an osmotic pressure gradient across the wall against an external fluid;
(c) a second compartment comprising a drug formulation that exhibits an osmotic pressure gradient across the wall against an external fluid;
(d) a film positioned between the first compartment and the second compartment, said film comprising means for forming at least one aperture in situ in the film during operation of the device; and, (e) at least one passageway in the wall communications with the first compartment and the exterior of the device.

20. The osmotic therapeutic device for the controlled delivery of beneficial drugs according to claim 19, wherein when the device is in operation in the environment of use, fluid from the environment is imbibed through the wall into (1) the first compartment in a tendency towards osmotic equilibrium at a rate determined by the permeability of the wall and the osmotic pressure gradient across the wall, thereby forming a solution containing drug that is delivered through the pasageway from the device at a controlled rate over a prolonged period of time, and into (2) the second compartment in a tendency towards osmotic equilibrium at a rate determined by the permeability of the wall and the osmotic pressure gradient across the wall, thereby forming a solution containing drug that is released through an aperture in film and hence through the passageway at a controlled rate over a prolonged period of time.

21. The osmotic therapeutic device for the controlled delivery of beneficial drugs according to claim 19, wherein the drug formulation in the first compartment comprises a dosage unit amount of drug and an osmagent.

22. The osmotic therapeutic device for the controlled delivery of beneficial drugs according to claim 19, wherein the drug formulation in the second compartment comprises a dosage unit amount of drug and an osmagent.

23. The osmotic therapeutic device for the controlled delivery of beneficial drugs according to claim 19, wherein the first and second compartments contain different drugs.

24. The osmotic therapeutic device for the controlled delivery of beneficial drugs according to claim 19, wherein the device is adapted for oral administration for delivering drugs to the gastrointestinal tract.

25. The osmotic therapeutic device for the controlled delivery of beneficial drugs according to claim 19, wherein the semipermeable lamina faces the compartments and the microporous lamina faces the environment.

26. The osmotic therapeutic device for the controlled delivery of beneficial drugs according to claim 19, wherein the microporous lamina faces the compartments and the semipermeable lamina faces the environment.

27. A method of delivering a first drug to the stomach and the intestine and a second drug to the colon of a warm-blooded animal, wherein the method comprises:
(a) admitting into the gastrointestinal tract of a warm-blooded animal a dispensing device comprising:
(1) a wall comprising a semipermeable composition permeable to the passage of an exterior fluid present in the gastrointestinal tract and substantially impermeable to the passage of a beneficial drug, which wall surrrounds;
(2) a first compartment consisting a first drug delivery in the stomach and the small intestine of the gastrointestinal tract;
(3) a second compartment comprising a second drug for delivering in the colon of the gastrointestinal tract;
(4) at least one passageway in the wall communicating with the first compartment and the exterior of the device;
(5) a partition in the device separating the first and second compartments, said partition forming at least one drug releasing aperture when the device is delivering drug;
(b) delivering the first drug by the device imbibing fluid through the wall into the compartment to form a solution containing drug that is delivered through a passageway to the stomach and the small intestine; and,
(c) delivering the second drug by the device imbibing fluid through the wall into the compartment to form a solution containing drug with the partition forming an aperture in situ for delivering the drug from the compartment and through the passageway to the colon.

28. A method for delivering a drug to the colon of an animal, which method comprises:
(a) admitting into the gastrointestinal tract of an animal an osmotic dispensing device comprising:
(1) a wall comprising a composition permeable to the passage of fluid and substantially impermeable to the passage of a drug, said wall surrounding;
(2) an internal lumen, which lumen comprises:
(A) a first area containing a nontoxic therapeutically inactive osmotic composition;
(B) a second area containing a nontoxic therapeutically active drug composition;
(C) means in the lumen for separating the first and second area and for releasing drug composition from the second area; and,
(3) delivering the drug by (i) first delivering the osmotic composition through the passageway, (ii) the means releasing the drug from the second area, and (iii) delivering the drug through the passageway to the colon.

29. The osmotic therapeutic device for the controlled delivery of a beneficial drug to a biological environment according to claim 20, wherein the microporous lamina comprises from 5 to 70% of a pore former that is a member selected from the group consisting of sucrose, glucose, fructose, mannitol, mannose, galactose and sorbitol, which pore former is removed from the lamina in the environment of use for providing at least one pore comprising an opening on both faces of the lamina that is a means and method suitable for releasing a beneficial drug.

* * * * *